Figure 1:
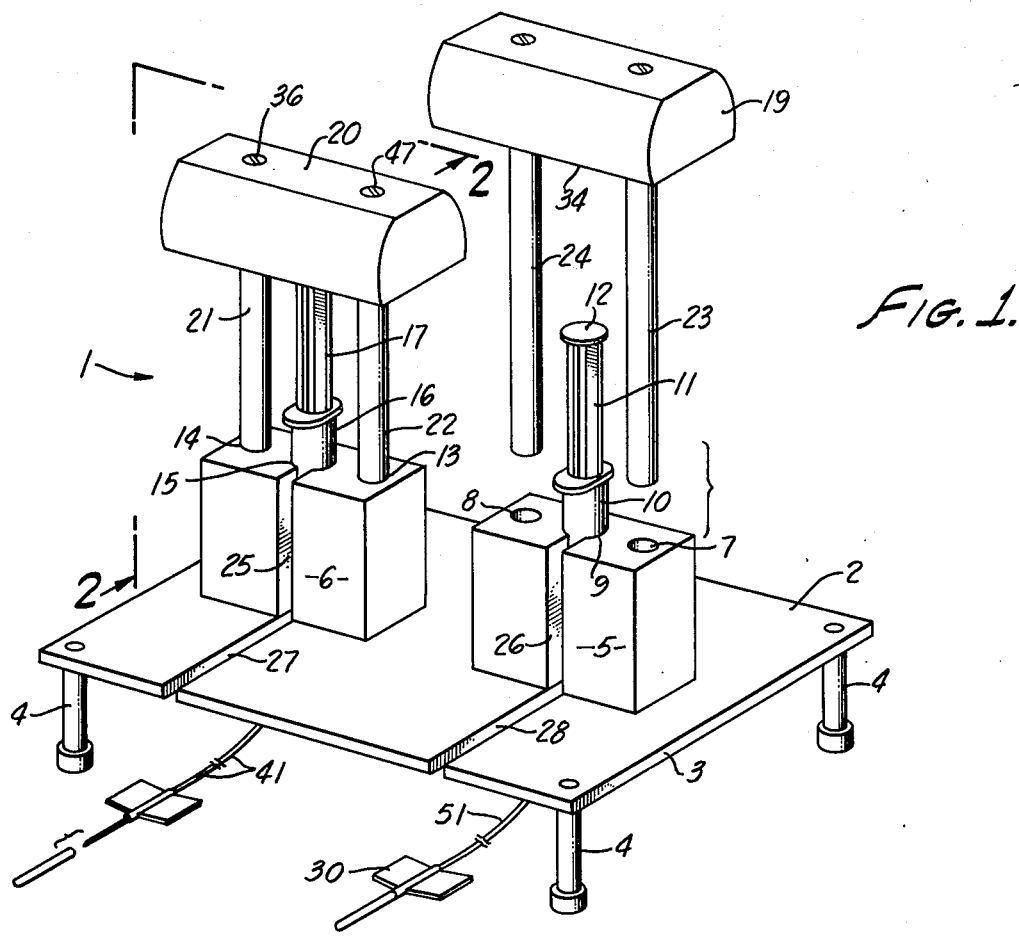

United States Patent [19]
Puccio

[11] 4,132,231
[45] Jan. 2, 1979

[54] INJECTION DEVICE

[76] Inventor: Vincent Puccio, 245 N. Cresta Ave., North San Gabriel, Calif. 91775

[21] Appl. No.: 798,795

[22] Filed: May 20, 1977

[51] Int. Cl.² .............................................. A61M 5/00
[52] U.S. Cl. ............................ 128/218 A; 128/214 F; 128/DIG. 12
[58] Field of Search ............... 128/218 R, 218 A, 272, 128/DIG. 1, DIG. 12, 214 R, 214 F, 215, 216, 2 A

[56] References Cited
U.S. PATENT DOCUMENTS

| 3,017,883 | 1/1962 | Dickinson, Jr. | 128/272 |
| 3,472,226 | 10/1969 | Haber | 128/218 R |

*Primary Examiner*—John D. Yasko
*Attorney, Agent, or Firm*—Patrick F. Bright

[57] ABSTRACT

An injection device especially useful in the injection of radio-opaque fluids into humans and animals under continuous pressure includes a pair of blocks mounted side-by-side on a planar base that is supported by legs mounted below the base near its corners. Each block includes a syringe holding passage flanked by a pair of passages shaped to receive rods joined to a weight of predetermined size. The syringe holding passage is narrowed at the bottom to preclude passage of the syringe completely therethrough, but has an opening sufficiently large to permit passage of a needle or a catheter and needle joined to the discharge end of the syringe.

A slot extends from the outer surface of each block into the syringe holding passage in that block and extends along the length of the passage and through the base means to permit means joined to the discharge end of the syringe to pass through the block and the base from above the base.

8 Claims, 3 Drawing Figures

U.S. Patent      Jan. 2, 1979      4,132,231

INJECTION DEVICE

This invention relates to a device for injecting fluids, particularly radio-opaque fluids, into humans and animals. More particularly, this invention relates to a device for injecting fluids into humans and animals under constant pressure from a pair of syringes simultaneously but separately, and at rates of delivery that may, if desired, differ.

Many prior art devices are available for injecting radio-opaque fluids into humans and animals from syringes. However, most are unstable, difficult or impossible to sterilize, have so many moving parts as to be constantly in need of repair or adjustment, or have some other defect. Some of these devices are shown in the following U.S. Pat. Nos. 1,159,127; 2,693,801; 2,786,468; 3,865,371; 3,151,616; 3,153,414; 3,451,393; 3,456,649; 3,565,292; 3,647,117; 3,674,009; and 3,886,938.

This invention relates to an injection device especially suitable for injecting fluids such as radio-opaque fluids into humans and animals under continuous pressure from a plurality of syringes simultaneously at the same rate of delivery or at different rates of delivery. The device comprises base means and block means joined preferably fixedly in upright posture to said base means. The block means includes at least one passage means therein for receiving and holding a syringe firmly upright therein, and weight means for exerting pressure on the plunger of the syringe. Each weight means includes guiding means received in guide passage means in the block means for directing the force of the weight means continuously upon the plunger of the syringe. Preferably, the block means comprises two separate blocks, each including a syringe holding passage and guide passage means. This permits injection of fluids from two separate syringes simultaneously, in overlapping time periods, in contiguous periods or in staggered periods. This also permits the use of a separate weight for depressing each syringe, which in turn allows different fluid injection rates or similar rates from different size syringes. Alternatively, the block means may simply be one block with two syringe holding passages for holding two separate syringes.

Each syringe holding passage must be sufficiently long to support the body of the syringe firmly upright, and each includes means for preventing the body of the syringe from passing completely through the block means. Preferably, the syringe holding passages pass completely through the block and through the base to which the block is joined. This permits the discharge end of the syringe to project to or beyond the base to permit the user of the device to reach and adjust means joined to that discharge end readily.

The weight means is a mass of predetermined size and weight sufficient to exert the desired pressure on the syringe plunger. Preferably, each weight means is a metal block, preferably having a shape that permits hand control. Joined to the weight means is guiding means that fit closely into guide passage means in the block means. With the guiding means inserted in the guide passage means, the force of the weight means is directed continuously upon the syringe plunger. Preferably, the guiding means are a pair of rods joined to the weight means and spaced sufficiently far apart to permit the syringe and its plunger to lie between the rods. This permits the surface of the weight means between the rods to impinge upon the top of the syringe plunger and to exert a continuous pressure upon the plunger in the linear path of the plunger through the syringe. Where the surface of the weight means that impinges on the syringe plunger is made of a substance such as metal, the surface may have affixed thereto a pad made of a substance such as rubber or plastic to increase the friction between the plunger and the surface of the weight means impinging on the plunger.

The preferred embodiment includes two separate block means, each block having its own weight means, each including one syringe holding passage and two guide passage means. This construction permits weight means of different sizes, and permits manipulation of the syringe beneath each weight means independently of the other. However, an alternative embodiment might include a single weight means applied to the plungers of two or more syringes simultaneously. Although the preferred embodiment includes two guide passage means, no more than one guiding means received in a single guide passage means in the block means is necessary. In such an embodiment, the guide passage means might, for example, lie between the plungers of two syringes in separate syringe holding passages.

Preferably, the base means is a planar plate, rectangular or square in shape. The base means preferably includes means for elevating the base means above and supporting the base means on a surface. These elevating means are preferably legs placed at or near the corners of the base means where the base is square or rectangular. The legs are preferably long enough to permit passing tubing or other discharge means attached to the syringes placed in the block means on the base means beneath the base means. To that end, the legs in the preferred embodiment are about 2 to about 3 inches long, which permits the user to readily reach and adjust any means attached to syringes below the base means.

The preferred embodiment also includes slot means through the block means into each syringe holding passage and slot means indexed thereto through the base means to permit passage of means joined to a syringe therethrough. This permits passing means joined to the discharge end of the syringe through the syringe holding passage from above the device and out from beneath the base to which the block means is joined.

Figure 2:
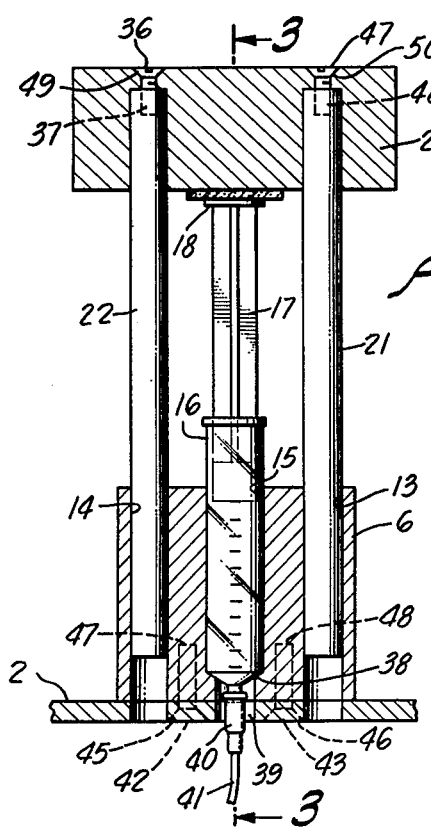
Figure 3:
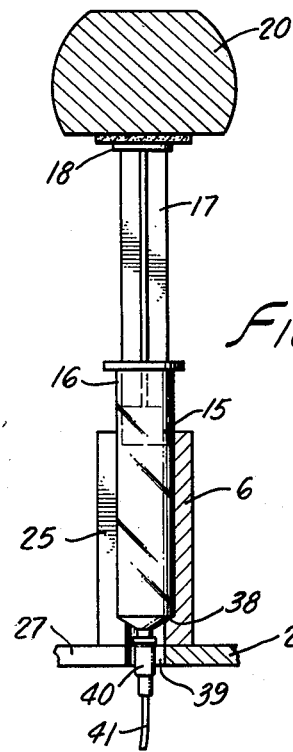

Referring now to the drawings,

FIG. 1 shows the preferred embodiment of the invention with a pair of blocks mounted on a single planar base;

FIG. 2 shows a cross-sectional view of the embodiment pictured in FIG. 1, taken along line 2—2 in FIG. 1; and FIG. 3 shows a sectional view of the embodiment shown in FIGS. 1 and 2 taken along the line 3—3 in FIG. 2.

In the drawings, the injection device includes a planar base 2 preferably made of steel having a thickness 3 in the range of about 0.25 to about 1.0 inch. Joined to each of the corners of base 2 are legs 4, which may be in the range of about 2 to about 3 inch long, and which serve to elevate the base means 2 above and support base means 2 on a surface.

Joined to base 2 are block means 5 and 6 including syringe receiving and holding passage means 9 and 15, respectively. Removably fitted within and firmly held upright in passages 9 and 15 are syringes 10 and 16 plungers 11 and 17 terminating in pressure plates 12 and 18, respectively. As best seen in FIGS. 2 and 3, passage 15 passes completely through block 6, and is sufficiently large in diameter along most of its length to permit the body of syringe 16 to pass nearly completely through. However, syringe holding passage 15 is of narrower cross section 38 near the bottom thereof and this narrowed cross section precludes passage of the syringe completely therethrough. As FIGS. 2 and 3 show, the narrowed portion 39 of passage means 15 permits the discharge end 40 of syringe 16 to project downwardly therethrough which permits adjustment of tubing 41 attached to discharge end 40.

Block means 5 includes cylindrical guide passage means 7 and 8 that are of sufficient size and shape to receive guiding means 23 and 24 joined to weight means 19. Guiding passage means 7 and 8 lie on opposite sides of syringe holding and receiving passage 9 and insertion of guiding means 23 and 24 therein brings planar surface 34 of weight means 19 to bear upon pressure plate 12 of syringe plunger 11. Weight means 19 exerts positive continuous pressure upon plunger 11 to effect continuous delivery of the fluid in syringe 10 through tubing 51 and catheter assembly 30.

Similarly, block means 6 includes guide passage means 13 and 14 for receiving guiding means 22 and 21, respectively, that are joined to weight means 20. The planar surface of weight means 20 between guiding means 22 and 21 exerts continuous positive pressure on thumb plate 18 of plunger 17 in syringe 16. Because guiding means 21, 22, 23 and 24 are shaped to fit closely within guide passage means 7, 8, 13 and 14, yet move smoothly through these passages, injection device 1 reliably applies the force of weight means 19 and 20 to plungers 11 and 17 through the force of gravity. This precludes the need for a power source and potential breakdown of the device where power failures occur, mechanical or electrical failures develop in the device or some combination of the foregoing might disable prior art devices.

FIG. 2 shows that block means 6 is joined to base means 2 through screws 42 and 43 that fit through openings 45 and 46 in base 2 and thread into holes 47 and 48 in the bottom of block 6. Weight means 20 is joined to guiding means 21 and 22 by means of screws 36 and 47 that fit into countersunk openings 49 and 50 in the top surface of weight means 20 and thread into threaded openings 37 and 48, respectively, in weight means 20. Weight means 19 is similarly joined to guiding means 23 and 24. This construction permits changing the weight means for weights of different size, shape or both, disassembling them for cleaning, and the like.

Block means 5 includes slot means 26 along the length of syringe holding passage 9 that extends from the outer surface of block 5 into the syringe holding passage 9. Slot means 26 is indexed with slot means 28 in base means 2 to permit the passage of means joined to syringe 10 through the block means 5 and base means 2 to eliminate the awkwardness of attaching such means to the syringe from beneath base means 2. Similarly, block 6 is fitted with slot means 25 which indexes with slot means 27 in base means 2 for the same purpose. In the embodiment as shown, slot means 25 and 27 are wide enough to permit passage of tubing 41 appended to the dishcarge end of syringe 16. Similarly, slot means 26 and 28 are wide enough to permit passage of tubing means 51 joined to syringe 10.

What is claimed is:

1. An injection device comprising base means and block means joined in upright posture to said base means, said block means including at least one passage means in said block means for receiving and holding at least one syringe therein, said syringe holding passage means including means for preventing passage of the syringe completely therethrough, but for permitting passage therethrough of means of smaller cross-sectional area than the syringe, and weight means comprising a mass of predetermined weight for exerting pressure on the plunger of said syringe, said weight means including guiding means received in guide passage means in said block means for directing the force of the weight means by gravity alone continuously upon said plunger, said guiding means comprising at least one rod adapted to pass sufficiently far into said guide passage means to permit said mass to depress the plunger of said syringe, and said syringe holding passage means and the base means including slot means for permitting passage of means joined to the syringe through said base means and through said block means into said syringe holding passage means.

2. The device of claim 1 including two separate block means each including one syringe holding passage and two guide passage means and each block having a weight means therefor.

3. The device of claim 1 wherein said base means includes means for elevating said base means above and supporting said base means on a surface.

4. The device of claim 3 wherein the elevating means comprises legs joined to said base means.

5. The device of claim 4 wherein the base means is rectangular or square and said legs project downwardly from near each corner of said base.

6. The device of claim 2 wherein said two guide passage means in each block are on opposite sides of the syringe holding passage means in that block.

7. The device of claim 6 wherein each guide passage means passes completely through said block.

8. The device of claim 1 wherein the device includes two weight means of different predetermined weights, each weight means is received in separate block means, and each operates independently of the other weight means.

* * * * *